United States Patent [19]

O'Lenick, Jr. et al.

[11] Patent Number: 4,800,077

[45] Date of Patent: Jan. 24, 1989

[54] GUERBET QUATERNARY COMPOUNDS

[75] Inventors: A. J. O'Lenick, Jr.; Wayne C. Smith, both of Lilburn, Ga.

[73] Assignee: GAF Corporation, Wayne, N.J.

[21] Appl. No.: 143,570

[22] Filed: Jan. 13, 1988

[51] Int. Cl.[4] .................................................. A61K 7/09
[52] U.S. Cl. ...................................... 424/70; 252/8.8; 260/404.5; 540/451; 540/553; 544/335; 548/354; 548/951
[58] Field of Search ..................... 564/505, 294; 260/404.5 Q, 404.5 EO; 540/451, 553; 544/242, 335; 548/336, 951, 341, 351; 252/8.8; 424/70

[56] References Cited

U.S. PATENT DOCUMENTS

| | | | |
|---|---|---|---|
| 3,445,440 | 5/1969 | Susi et al. | 524/140 |
| 3,517,045 | 6/1970 | Susi et al. | 564/281 |
| 4,144,122 | 3/1979 | Emanuelsson et al. | 162/158 |
| 4,215,064 | 7/1980 | Lindemann et al. | 558/86 |
| 4,283,541 | 8/1981 | Shroff et al. | 546/336 |
| 4,731,190 | 3/1988 | O'Lenick | 252/49.3 |

Primary Examiner—Joseph L. Schofer
Assistant Examiner—Jeffrey T. Smith

Attorney, Agent, or Firm—Marilyn J. Maue; Joshua J. Ward

[57] ABSTRACT

The present invention deals with novel quaternary compounds and their application as softening, anti-tangle, and conditioning agents. The properties of these novel quaternary compounds which make them well suited for these applications is their substantivity to fibers, hair and skin and that they are very mild to the skin and eyes.

The compounds of the invention conform to the formula:

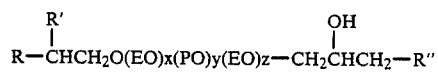

wherein:
  R is $C_6$ to $C_{20}$;
  R' is the same or different than R and is from $C_6$ to $C_{20}$,
  EO is an ethylene oxide residue;
  PO is a propylene oxide residue;
  x,y,z are integers and independently are from 0 to 10.

11 Claims, No Drawings

GUERBET QUATERNARY COMPOUNDS

BACKGROUND OF THE INVENTION

The present invention deals with the composition, and application of novel quaternary compounds, as softening, anti-tangle, and conditioning agents for use in personal care, textile and related applications. The properties of these novel quaternary compounds which makes them well suited for these applications is the fact that they are substantive to fibers, hair and skin and also very mild to the skin and eyes.

Standard quaternary compounds are prepared by quaternization of a tertiary amine with such agents as benzyl chloride or di-methyl sulfate or di-ethyl sulfate or methyl chloride. These materials are relatively inexpensive but offer several key disadvantages. These include yellowing of fabrics, a tendency to build-up upon repeated treatment, and variability in hand (i.e. softness and feel). Standard softeners used are selected from the following classes:

Class #1. Alkyl Imidazoline Quaternary Compounds made from the quaternization of an imidazoline made by reacting diethylenetriamine, and a high molecular weight fatty acid such as stearic acid. The standard quaternizing agents are di-ethyl sulfate, or methyl chloride, or di-methyl sulfate, or methyl chloride or benzyl chloride.

Class #2. Alkyl or dialkyl tertiary amines quaternized with benzyl chloride or di-ethyl sulfate or methyl chloride or di-methyl sulfate Class #3. Quaternary compounds of ethoxylated, propoxylated or nonalkoxylated amido amines derived from the reaction of a high molecular weight fatty acid like stearic acid and a polyamine like diethylene triamine. The standard quaternizing agents are di-ethyl sulfate or di-methyl sulfate or methyl chloride or benzyl chloride.

Class #4. Amido amine salts derived from partially acid neutralized amines.

It is known that under certain catalytic conditions, epichlorohydrin reacts with certain alcohols to give an intermediate which can be used to react with tertiary amines to quaternary compounds, U.S. Pat. No. 3,445,440 to Susi (May 1969) and U.S. Pat. No. 3,517,045 to Susi (June 1970) teaches the use of chlorohydroxypropyl ether to alkylate specific tertiary amines which are the reaction product of a primary fatty amine and ethylene or propylene oxide to give compounds conforming to the following structure;

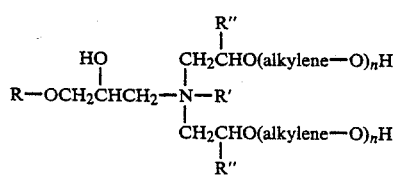

The above compounds are used as antistatic agents in polymeric compositions such as polyolefin. The antistatic properties of these compounds are achieved by the minimization of static charges on the polymer surface. These anti-static materials are incorporated into the polymer melt and are effective by virtue of their insolubility in the molten polymer. The quaternary compounds migrate to the polymer surface and are effective antistatic agents.

U.S. Pat. No. 4,144,122 to Emanuelsson issued Mar. 13, 1979 teaches that tallow alcohol and certain other higher molecular weight non-guerbet alcohols and their alkoxylates can be reacted with epichlorohydrin, then subsequently with tertiary amines to give compounds suitable for paper debonding.

U.S. Pat. No. 4,215,064 to Lindemann et al issued July 29, 1980 teaches that phosphobetaines can be prepared by the reaction of a phosphate or phosphite salt with epichlorohydrin under aqueous conditions. U.S. Pat. No. 4,283,541 to Shroff et al, issued Aug. 11, 1981 teaches the process for the preparation of the phosphobetaines described in Lindemann (4,215,064). None of these patents teach the compounds of the present invention.

A surprising feature of the compounds of the present invention is their liquid nature and mild nature to skin and eye. This makes the materials of the present invention very useful in personal care products. It is the use of guerbet alcohols with their unique branching and the alkoxylates of the guerbet alcohols that results in these highly desirable properties. Neither the Susi nor the Emanuelsson patents make use of guerbet alcohols nor their alkoxylates. Nor are the low irritation properties or liquidity expected from the teachings of the Susi patents or the Emanuelsson patent.

It is the object of this invention to produce high molecular weight quaternary compounds that have improved liquidity and are free of the undesirable by-products found in the more irritating standard quaternary compounds. This improved performance and retained liquidity relates to the fact that guerbet alcohols, with their specific branching pattern allows for the use of a high molecular weight hydrophobe which is less likely to irritate. The use of guerbets through the reaction of that alcohol with ethylene oxide and/or propylene oxide, and the reaction with epichlorohydrin to give a hydroxypropyl linkage, results in the desired high molecular weight quaternary compounds of this invention.

The references cited herein are incorporated by reference to the extent applicable. Ratios and percentages are by weight and temperatures are Celsius unless otherwise stated.

THE INVENTION

The quaternary compounds of the invention conform to the following generic formula;

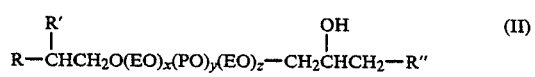

wherein:
R is from $C_6$ to $C_{20}$,
R' is the same or different than R and is selected from $C_6$ to $C_{20}$.
EO is an ethylene oxide residue
PO is a propylene oxide residue
x, y, z are integers and independently may be from 0 to 10;
R" is selected from;

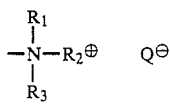  (III)

wherein;
R1, R2, and R3 are each independently selected from $C_1$ to $C_{20}$.
Q is a anion needed for charge balance and is selected from halide or sulfate, preferably chloride.
Additionally R" may be alkylamido conforming to the following structure:

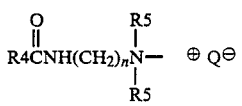  (IV)

wherein
R4 is selected from $C_6$ to $C_{20}$;
R5 is a lower alkyl, preferably selected from methyl or ethyl;
n is an integer from 1 to 5;
additionally R" may be a heterocycle and conforms to the following structure;

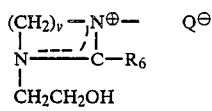  (V)

wherein
R6 is selected from $C_6$ to $C_{20}$,
v is an integer from 1 to 5.
The preferred compounds of the invention conform to the following generic structure:

wherein
R and R' are selected from $C_{10}$ to $C_{18}$ and are saturated;
x, y, z are integers and independently may are from 1 to 8;
R" is a heterocycle and conforms to the following structure;

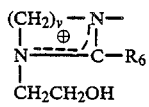

wherein
R6 is $C_{16}$ to $C_{18}$ and is saturated.
v is 2.

APPLICATIONS OF THE COMPOUNNDS OF THE INVENTION

Compounds of this invention were compared to standard compounds commercially available using AATCC Test Method 117-1979. The color fastness heat test uses a 400 F. (205 F.) hot iron which is applied for 60 and 180 seconds. The color is rated on a 1-5 basis for yellowness, (5 being the most yellow).

| Compound | CAS Number | Yellowness |
| --- | --- | --- |
| Class #1 Compound | 68122-86-1 | 4 |
| Class #2 Compound | 61789-81-9 | 4 |
| Class #3 Compound | 65098-88-6 | 5 |
| Class #4 Compound | 68308-45-2 | 4 |
| Developmental #20 | | 1 |
| Developmental #22 | | 2 |

The compatibility of these novel compounds 20 and 22 with animal tissue was tested. In these tests a 0.1 ml sample of the material being tested was introduced into one eye of an albino rabbit, the other eye serves as a control. Observations were made after 1 day, 2 days, 3 days, 4 days and 7 days. Second and third instillations were made after 24 and 48 hours. Results can vary from substantially no change to complete corneal opacity. Ocular lesions are scored for the cornea, iris and conjuctiva on a scale of 1 to 6 with the higher score indicating graded ocular irritation. The scores are added for the six rabbits tested and an average is obtained. Typical results for the standard quaternary compound used in hair conditioning (stearyldimethylbenzyl ammonium chloride) and a representative of the new compounds being tested are as follows;

| Ocular Irritation | | | | | |
| --- | --- | --- | --- | --- | --- |
| 1 | 2 | 3 | 4 | 7 | |
| | | Days | | | Dermal Irritation |
| Developmental Compound #21 | | | | | |
| 2 | 1 | 0 | 0 | 0 | 0.80 |
| Comparison Product | | | | | |
| Stearyldimethylbenzyl ammonium chloride | | | | | |
| 34 | 29 | 27 | 26 | 26 | 3.75 |

The data shows dramatically that the novel quaternary compounds are very mild, while the standard quaternary used in hair conditioning is a severe irritant.

WET COMB OUT TEST

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
| --- | --- |
| Product | Test in Seconds |
| Product Example #20 | 11 |
| Product Example #22 | 13 |
| Stearyldimethylbenzyl | 12 |

| Rinse Conditioner (Wet Comb Out Test) | |
|---|---|
| Product | Test in Seconds |
| ammonium chloride | |

As can be seen, the compounds of the invention give significant conditioning properties to hair, and coupled with their mild nature with regard to skin and eyes, makes it a prime candidate for cosmetic applications.

Guerbet Alcohols have been known since the 1890's when Marcel Guerbet first synthesized these materials (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

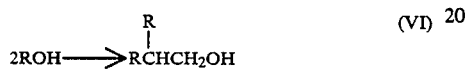

As can be seen by the above reaction the molecules have substitution on the second carbon from the hydroxyl group. This branching has been found to be critical to the preparation of a product having the desired properties. If the branching were on the same carbon as the hydroxyl group, the hydroxyl group would be a secondary one and would be very hindered and has low reactivity. As one moves the branch position away from the beta carbon, the liquidity, and substantivity to hair and fiber decreases.

Guerbet alcohols that are the reaction product of one specific raw material alcohol will result in a so called "homo-guerbet". In this case R and R' are identical. If the starting alcohols used in the guerbet reaction are of differing molecular weights a so called "hetero-guerbet" results. This type of guerbet has a mixed distribution of all possible combinations of alcohols. For this reason R and R' in the generic formula may be the same or different.

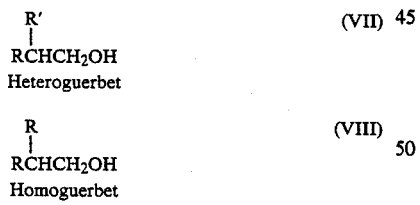

EXAMPLES OF GUERBET ALCOHOL

Example 1

Guerbet Alcohol

To 967 grams of decyl alcohol in a suitable reation flask, add 30.0 grams of potassium hydroxide and 2.0 grams of nickel, under good agitation. Heat material to 250 degrees C. as rapidly as possible. The water generated from the reaction will separate from the refluxing alcohol and is removed from the reaction mass. Reaction progress is followed by gas chromatographic analysis. The amount of $C_{20}$ guerbet will exceed 90%. The reaction is then cooled, filtered and distilled to give the commercial guerbet.

Example 2

To 500 grams of decyl alcohol and 500 grams of lauryl alcohol in a suitable reaction flask, add 30.0 grams of potassium hydroxide and 2.0 grams of zinc oxide, under good agitation. Heat material to 250 C. as rapidly as possible. The water generated from the reaction will separate from the refluxing alcohol and is removed from the reaction mass. Reaction progress is followed by gas chromatographic analysis. The guerbet obtained will exceed 90%. The reaction mass is then cooled, filtered and distilled to give the commercial guerbet.

Example 3

To 500 grams of decyl alcohol and 500 grams of octyl alcohol in a suitable reaction flask, add 30.0 grams of potassium hydroxide and 2.0 grams of nickel, under good agitation. Heat material to 250 degrees C. as rapidly as possible. The water generated from the reaction will separate from the refluxing alcohol and is removed from the reaction mass. Reaction progress is followed by gas chromatographic analysis. The guerbet obtained will exceed 90%. The reaction is then cooled, filtered and distilled to give the commercial guerbet.

Example 4

To 1000 grams of octyl alcohol in a suitable reaction flask, add 30.0 grams of potassium hydroxide and 2.0 grams of nickel, under good agitation. Heat material to 250 C. as rapidly as possible. The water generated from the reaction will separate from the refluxing alcohol and is removed from the reaction mass. Reaction progress is followed by gas chromatographic analysis. The yield of $C_{16}$ alcohol will exceed 90%. The reaction is then cooled, filtered and distilled to give the commercial guerbet.

Example 5

To 967 grams of isodecyl alcohol and 500 tridecyl alcohol in a suitable reaction flask, add 30.0 grams of potassium hydroxide and 2.0 grams of nickel, under good agitation. Heat material to 250 C. as rapidly as possible. The water generated from the reaction will separate from the refluxing alcohol and is removed from the reaction mass. Reaction progress is followed by gas chromatographic analysis. The guerbet yield will exceed 90%. The reaction is then cooled, filtered and distilled to give the commercial guerbet.

Example 6

To 976 grams of coco alcohol ($C_{12-16}$ mixture) in a suitable reaction flask, add 30.0 grams of potassium hydroxide and 2.0 grams of nickel, under good agitation. Heat material to 250 C. as rapidly as possible. The water generated from the reaction will separate from the refluxing alcohol and is removed from the reaction mass. Reaction progress is followed by gas chromotographic analysis. The % conversion to the guerbet will exceed 90%. The reaction is then cooled, filtered and distilled to give the commercial guerbet.

Additionally, guerbet alcohols are commercially available from Exxon and Henkel.

PREPARATION OF THE HYDROXYPROPYLETHER HALIDE

General Procedure

Place the indicated amount of the guerbet alcohol produced by the example shown in a suitable vessel. Add the desired amount of catalyst as shown under good agitation and a nitrogen sparge. The specified amount of epichlorohydrin is added. A molar excess of 0.1 to 0.5 of epichlorohydrin is added. The temperature is held between 100–125 degrees C. for two to six hours. The excess epichlorohydrin is stripped off under vacuum. Reaction progress is monitored by percent epoxide analysis and after stripping is very small.

| | | Grams | | | |
|---|---|---|---|---|---|
| | Guerbet | Guerbet | Epichloro- | Catalyst | |
| Example | Alcohol | Alcohol | hydrin | BF3 | SnCl4 |
| 7 | Examp. 1 | 719.0 | 281.0 | 0 | 2 |
| 8 | Examp. 2 | 752.0 | 248.0 | 4 | 0 |
| 9 | Examp. 3 | 700.0 | 300.0 | 0 | 2 |
| 10 | Examp. 4 | 675.0 | 325.0 | 4 | 0 |
| 11 | Examp. 5 | 750.0 | 250.0 | 0 | 4 |
| 12 | Examp. 6 | 752.0 | 248.0 | 2 | 0 |

Alkoxylation of the Guerbet

To 500.0 grams of the guerbet alcohol produced according to the specified example is added 2.0 g KOH in a suitable vessel. The specified amount of ethylene oxide and/or propylene oxide is then added at 110–120 C. Subsequently, 2 grams of tin tetrachloride under a nitrogen blanket and good agitation. The specified amount of epichlorohydrin is then added slowly over two hours. The temperature is held between 60 and 120 degrees C. for two to six hours. Finally, the excess epichlorohydrin is stripped off under vacuum.

| | | Grams | | |
|---|---|---|---|---|
| | Guerbet | Ethylene | Propylene | Epichloro- |
| Example | Alcohol | oxide | oxide | hydrin |
| 13 | Examp. 1 | 170.0 | 0 | 150.0 |
| 14 | Examp. 2 | 493.0 | 0 | 130.0 |
| 15 | Examp. 1 | 170.0 | 170.0 | 130.0 |
| 16 | Examp. 2 | 151.2 | 112.5 | 130.0 |

PREPARATION OF THE QUATERNARY COMPOUNDS

Example 17

To 643.0 grams of the hydroxypropyl halide (example 7) is added to 2,000 grams of water and 356.0 grams of lauryl dimethyl amine (ADMA 2 Ethyl Corp.) under good agitation and a nitrogen blanket. The reaction mass is heated to 80–90 C., and held in this range until the amount of inorganic chloride reaches a minimum of 97% of theoretical.

Example 18

To 740.0 grams of the hydroxypropyl halide (example 13) is added to 2,000 grams of water and 260.0 grams of lauryl dimethyl amine (ADMA 2 Ethyl Corp.) under good agitation and a nitrogen blanket. The reaction mass is heated to 80–90 C., and held in this range until the amount of inorganic chloride reaches a minimum of 97% of theoretical.

Example 19

To 770.0 grams of the hydroxypropyl halide (example 16) is added to 2,000 grams of water and 230.0 grams of lauryl dimethyl amine (ADMA 2 Ethyl Corp.) under good agitation and a nitrogen blanket. The reaction mass is heated to 80–90 C., and held in this range until the amount of inorganic chloride reaches a minimum of 97% of theoretical.

Example 20

To 680.0 grams of the hydroxypropyl halide (example 7) is added to 2,000 grams of water and 320.0 grams of 1-hydroxyethyl-2-cocoimidazoile (Alkaline C) under good agitation and a nitrogen blanket. The reaction mass is heated to 80–90 C., and held in this range until the amount of inorganic chloride reaches a minimum of 97% of theoretical.

Example 21

To 637.6 grams of the hydroxypropyl halide (example 13) is added to 2,000 grams of water and 362.4 grams of bis-2-hydroxyethyl tallow amine (Alkaminox T-2), under good agitation and a nitrogen blanket. The reaction mass is heated to 80–90 C., and held in this range until the amount of inorganic chloride reaches a minimum of 97% of theoretical.

Example 22

To 564.0 grams of the hydroxypropyl halide (example 13) is added to 2,000 grams of water and 436.0 grams of cocamidopropyl dimethyl amine (Alkamide CAP), under good agitation and a nitrogen blanket. The reaction mass is heated to 80–90 C., and held in this range until the amount of inorganic chloride reaches a minimum of 97% of theoretical.

The quaternary compounds of this invention can be formulated into softeners that are applied directly in aqueous solution by themselves or formulated with anionic, nonionic or amphoteric surfactants and builders to prepare finished conditioner/detergent systems. The level of the quaternary of the present invention is typically used at a weight ratio to water of about 1:10:000 to 1:20 to soften fabric. Conditioners and Shampoos using the quaternary employ it at 2% to 30% by weight. Anionic surfactants include lauryl and stearyl sulfate as well as alkylbenzene sulfonates, preferably the sodium salts. Nonionic surfactants include alkylalkoxylates typically having from 10 to 20 carbon atoms in the alkyl group and from 1 to 10 alkylene oxide units (preferably ethylene). Builders include alkylene oxide units (preferably ethylene). Builders include the phosphates STPP and SPP as well as aluminosilicates.

What is claimed:

1. A compound conforming to the formula:

wherein;

R is $C_6$ to $C_{20}$;

R' is the same or different than R and is from $C_6$ to $C_{20}$;

EO is an ethylene oxide residue;

PO is a propylene oxide residue;

x, y, z are integers and independently are from 0 to 10;

R" is selected from;

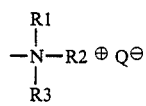

R1, R2, and R3 are each independently selected from $C_1$ to $C_{20}$;
Q is a anion needed for charge balance and is selected from halide or sulfate;
or R" may be alkylamido conforming to the following structure;

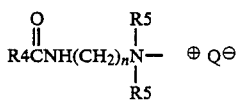

R4 is $C_6$ to $C_{20}$,
R5 is selected from methyl or ethyl,
n is an integer from 1 to 5;
Additionally R" may conform the structure;

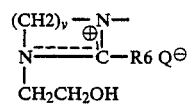

wherein
R6 is $C_6$ to $C_{20}$ and v is an integer from 1 to 5.

2. The compound of claim 1 wherein R" is;

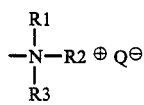

R1, R2, and R3 are alkyl and is selected from $C_3$ to $C_{18}$,
Q is a anion needed for charge balance and is selected from halide or sulfate.

3. The compound of claim 1 wherein;
R" conforms to the following structure;

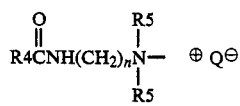 (IV)

wherein
R4 is $C_8$ to $C_{18}$,
R5 is selected from methyl or ethyl;
n is an integer from 1 to 5;

4. The compound of claim 1 wherein
R" is a heterocycle and conforms to the structure;

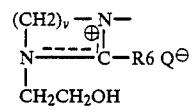

wherein
R6 is alkyl $C_8$ to $C_{18}$,
v is an integer from 2 to 4.

5. The compound of claim 1 wherein;
R and R' are each $C_{10}$;
x, y and z are each 0;
R" is

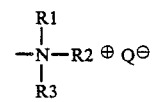

R1 is methyl, R2 is $C_{12}$, R3 is methyl, and Q is Cl.

6. The compound of claim 1 wherein:
R and R' are each $C_8$ to $C_{10}$, x=2, y=1, and z=1;
R" conforms to the following structure;

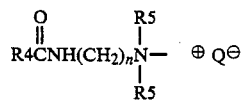

in
R4 is $C_{11}$ to $C_{17}$, R5 is methyl and n is 3.

7. The compound of claim 1 wherein:
R" conforms to the structure;

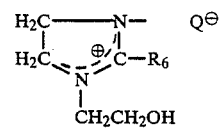

R6 is $C_{17}$.

8. The compound of claim 1 wherein R, R', R1, R2, and R3 are all alkyl.

9. The composition comprising an aqueous solution of the compound of claim 1 and a surfactant.

10. The compound of claim 1 used to treat hair or fabrics.

11. The compound of claim 1 used to treat celluose fibers.

* * * * *